(12) United States Patent
Zheng et al.

(10) Patent No.: US 10,792,275 B2
(45) Date of Patent: Oct. 6, 2020

(54) INHIBITING BINDING OF INFLUENZA-VIRUS PB2 SUBUNIT TO RNA CAP

(71) Applicant: Sinoclone Ltd., Hong Kong (CN)

(72) Inventors: Bojian Zheng, Vancouver (CA);
Shuofeng Yuan, Hong Kong (CN); Yi Tsun Richard Kao, Hong Kong (CN);
Jie Zhou, Hong Kong (CN)

(73) Assignee: Sinoclone Ltd, Hong Kong (CN)

( * ) Notice: Subject to any disclaimer, the term of this patent is extended or adjusted under 35 U.S.C. 154(b) by 122 days.

(21) Appl. No.: 16/093,529

(22) PCT Filed: Apr. 12, 2017

(86) PCT No.: PCT/CN2017/080241
§ 371 (c)(1),
(2) Date: Oct. 12, 2018

(87) PCT Pub. No.: WO2017/177919
PCT Pub. Date: Oct. 19, 2017

(65) Prior Publication Data
US 2019/0142785 A1     May 16, 2019

(30) Foreign Application Priority Data

Apr. 13, 2016   (CN) .......................... 2016 1 0232113

(51) Int. Cl.
| | | |
|---|---|---|
| *A61K 31/37* | (2006.01) | |
| *A61K 31/196* | (2006.01) | |
| *A61P 31/16* | (2006.01) | |
| *A61K 9/00* | (2006.01) | |

(52) U.S. Cl.
CPC ............ *A61K 31/37* (2013.01); *A61K 31/196* (2013.01); *A61P 31/16* (2018.01); *A61K 9/0043* (2013.01)

(58) Field of Classification Search
CPC ........ A61K 31/37; A61K 31/196; A61P 31/16
See application file for complete search history.

(56) References Cited

U.S. PATENT DOCUMENTS 8,633,198 B1     1/2014 Niazi et al.

FOREIGN PATENT DOCUMENTS

| CN | 101875946 A | 11/2010 |
|---|---|---|
| CN | 101970465 A | 2/2011 |
| CN | 104529987 B | 8/2016 |

OTHER PUBLICATIONS

Yuan, Shuofeng et al. "A novel small-molecule compound disrupts influenza A virus PB2 cap-binding and inhibits viral replication." J. Antimicrob. Chemother. 71 (2016): 2489-2497.
Wu, Shuangding et al. "In Silico Screening for PTPN22 Inhibitors: Active Hits from an Inactive Phosphatase Conformation." ChemMedChem 4 (2009): 440-444.
Bandyopadhyay, Chandrakanta et al. "Synthesis of Coumarin Derivatives from 4-Oxo-4H-1-benzopyran-3-carboxaldehyde via 3-(Arylaminomethylene)chroman-2,4-dione." Tetrahedron 56 (2000): 3583-3587.

*Primary Examiner* — James D. Anderson
(74) *Attorney, Agent, or Firm* — Stefan J. Kirchanski; Matthew J. Spark; Zuber Lawler & Del Duca LLP

(57) ABSTRACT

The present invention is a method of inhibiting the replication of an influenza virus by using an antiviral compound to inhibit the binding of an influenza-virus PB2 subunit to an RNA cap. The antiviral compound may be 5-iodo-2-[(3-methyl-4-nitrobenzoyl)amino]benzoic acid; 3,3'-[(4-methylphenyl)methylene]bis(4-hydroxy-2H-chromen-2-one); or 7-(4-hydroxy-2-oxo-2H-chromen-3-yl)-6H,7H,8Hchromeno[3,4':5,6]pyrano[3,2-c]chromene-6,8-dione. The aforementioned antiviral compounds have successfully inhibited the replication of influenza virus in vitro and in vivo in mouse models.

4 Claims, 3 Drawing Sheets

Figure 1

INHIBITING BINDING OF INFLUENZA-VIRUS PB2 SUBUNIT TO RNA CAP

CROSS-REFERENCE TO RELATED APPLICATIONS

Figure 2:
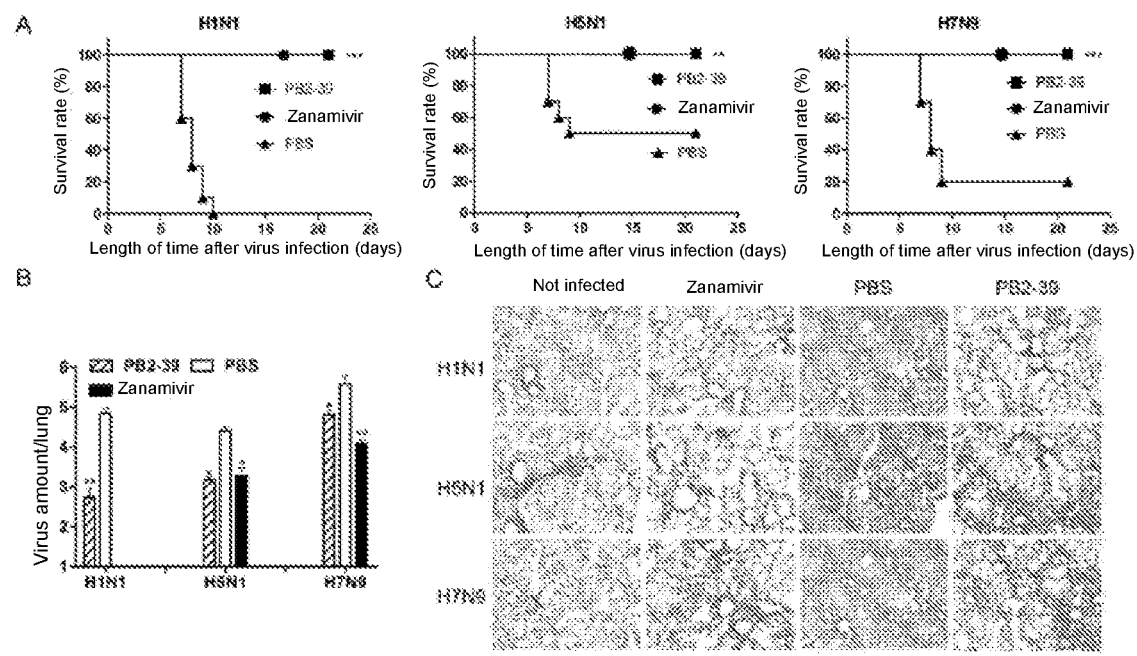

This application claims the priority of PCT Application No. PCT/CN2017/080241, filed on Apr. 12, 2017, which claims the priority of Chinese patent application No. 201610232113.3, filed on Apr. 13, 2016.

BACKGROUND OF THE INVENTION

Technical Field

The present invention relates to a compound that inhibits the binding of an RNA cap to an influenza-virus PB2 subunit.

Background Art

Influenza, which has high morbidity and mortality worldwide, is considered one of the most important viral threats to humans. Vaccination is the main way to control the spread of influenza virus. However, there are a number of limitations in the preparation of influenza vaccines, such as a delay of about six months between the identification of an outbreak of a new virus and the clinical application of a vaccine. Therefore, antiviral drugs are urgently needed for the prevention and treatment of influenza. Two types of antiviral drugs have been approved for clinical use, namely: M2 channel protein inhibitors (amantadine and rimantadine); and neuraminidase (NA) inhibitors (oseltamivir and zanamivir). However, the emergence of resistant strains, such as seasonal H3N2; 2009 type-A H1N1; H5N1; and H7N9 highly pathogenic avian influenza, has greatly weakened the clinical value of these two types of drugs. Therefore, new antiviral drugs that provide cross-protection between different subtypes of influenza virus have attracted much attention. The biological and structural functions of influenza's viral proteins have been extensively studied, resulting in more targets for the screening of drug candidates. In particular, the crystal structures of relevant functional domains of influenza-virus RNA polymerase have been successfully resolved. Because those proteins are quite conserved among different influenza subtypes, drugs designed or screened to target the functional domains of RNA polymerase are more likely to produce broad-spectrum antiviral effects against influenza.

Influenza-virus RNA polymerase is composed of three subunits: PA, PB1, and PB2. The ribonucleoprotein (RNP) formed by those subunits in combination with nucleoprotein (NP) is responsible for the transcription and replication of viral RNA in the nucleus of the host cell. In a process known as "cap-snatching," the transcription of viral mRNA depends first on the capture of a cap structure in the mRNA of the host cell by the PB2 subunit. Immediately thereafter, the PA subunit can use its endonuclease activity to cleave off an RNA sequence (e.g., a host mRNA sequence) downstream of the cap structure. The cleaved-off sequence is used as a primer for the transcription of the viral mRNA. Studies have shown that amino-acid residues 318-483 of the PB2 subunit form an RNA cap-binding domain (i.e., the PB2 cap-binding domain). That functional domain can bind the mRNA of a host cell by identifying its 5' cap structure. Since the PB2 cap-binding domain differs from the mode of mRNA cap-binding used by other proteins in the host cell, this factor suggests that drugs that inhibit the binding of the PB2 subunit to cap structures are unlikely to affect the normal use of cap structures by host cells.

Therefore, the PB2 cap-binding domain is a potential target for the screening of new antiviral drugs. In addition, studies have shown that amino-acid substitutions at key positions in the PB2 cap-binding domain significantly reduce the cap-binding activity of the PB2 subunit and the activity of the entire RNA polymerase. Therefore, the likelihood that drugs screened against the PB2 subunit will produce drug-resistant strains of virus is greatly reduced.

BRIEF SUMMARY OF THE INVENTION

The goal of the present invention is to overcome the shortcomings of the prior art by providing a compound capable of inhibiting the binding of influenza-virus PB2 subunits to RNA caps.

To achieve the aforementioned objective, the following technical approach is adopted: a compound capable of inhibiting the binding of an influenza-virus PB2 subunit to an RNA cap, the compound being one of the compounds shown in formula (I), formula (II), or formula (III). The compound shown in formula (I) is named 5-iodo-2-[(3-methyl-4-nitrobenzoyl)amino]benzoic acid and has the following structure:

(I)

The compound shown in formula (II) is named 3,3'-[(4-methylphenyl)methylene]bis(4-hydroxy-2H-chromen-2-one) and has the following structure:

(II)

The compound shown in formula (III) is named 7-(4-hydroxy-2-oxo-2H-chromen-3-yl)-6H,7H,8Hchromeno[3,4':5,6]pyrano[3,2-c]chromene-6,8-dione and has the following structure:

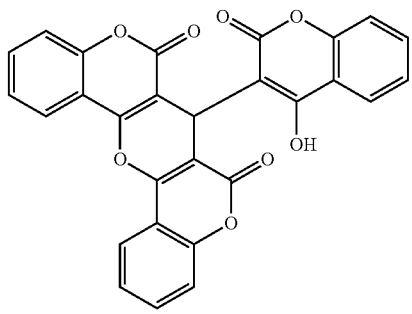

(III)

The compound shown in formula (I) is designated as PB2-19; the compound shown in formula (II) is designated as PB2-35; and the compound shown in formula (III) is designated as PB2-39. Each of the compounds shown in formulas (I), (II), and (III) of the present invention can interfere with binding of RNA caps to PB2 cap-binding domains of influenza viruses. Among those compounds, PB2-39 is the most effective inhibitor of influenza virus. PB2-39 can inhibit the replication in cells of multiple subtypes of influenza, including: H1N1; H3N2; H5N1; H7N7; H7N9; and H9N2. When BALB/c mice were infected with a lethal quantity of influenza virus and then treated with PB2-39 via nasal administration, their survival rate was significantly increased, and the amount of virus in their lung tissues was significantly reduced.

The present invention provides uses of the aforementioned compounds in preparing anti-influenza drugs.

The influenza virus is preferably at least one of influenza viruses A, B, and C.

The advantage of the present invention is to provide a compound as shown in formula (I), formula (II), or formula (III), which compound can inhibit the binding of influenza-virus PB2 subunit to RNA cap and have an anti-influenza effect.

BRIEF DESCRIPTION OF THE DRAWINGS

Figure 1:
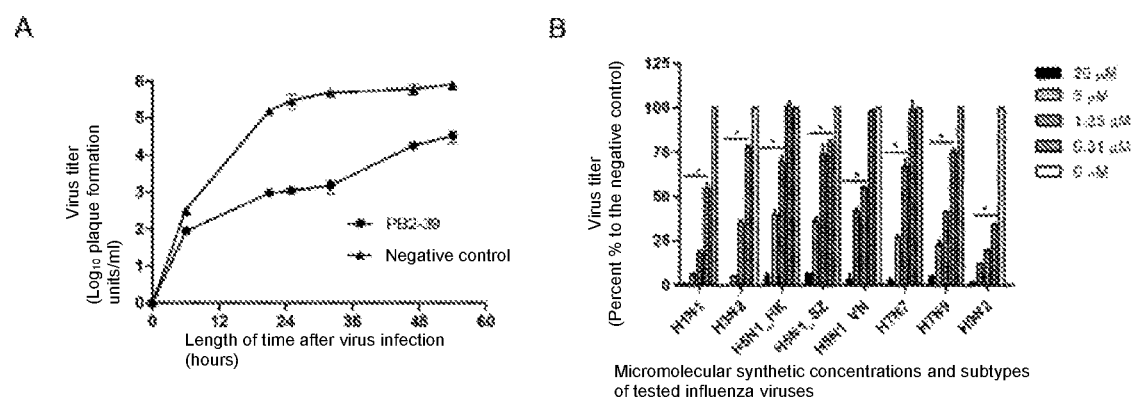

FIG. 1 shows the in vitro antiviral effect of PB2-39 according to embodiment 1 of the present invention.

FIG. 2 shows the antiviral effect of PB2-39 according to embodiment 1 of the present invention in mice.

FIG. 3 shows the antiviral effect of PB2-19 according to embodiment 1 of the present invention in mice.

DETAILED DESCRIPTION OF THE INVENTION

Specific Embodiments

In order to better illustrate the objectives, technical approach, and advantages of the present invention, the present invention will be further explained below in connection with specific embodiments.

Embodiment 1

1. Materials and Methods 1.1 Cells and Viruses

Madin-Darby canine kidney cells (MDCK cells) were cultured in Dulbecco's modified Eagle's medium (hereinafter "MEM," but also generally known as "DMEM") containing 10% heat-inactivated fetal bovine serum (FBS), 50 units/ml penicillin, and 50 μg/ml streptomycin. After being infected with the viruses, the MDCK cells were replaced in MEM containing 1 μg/ml of tosyl phenylalanyl chloromethyl ketone trypsin (TPCK trypsin) but without fetal bovine serum. A total of 8 strains/6 subtypes of influenza viruses, namely: A/HK/415742/09(H1N1); A/Hong Kong/1/1968(H3N2); A/Shenzhen/406H/2006 (H5N1_SZ); A/Hong Kong/156/97(H5NI_HK); A/Vietnam/1194/2004(H5N1_VN); A/Netherlands/219/2003(H7N7); A/Anhui/I/20I3(H7N9); and A/HK/I073/1999(H9N2), were identified, respectively cultured in the MDCK cells, and used in this study. Titers of the viruses were measured by plaque assays, and then the viruses were separated and stored at −80° C. All tests relating to live viruses were carried out in facilities with biosafety level 2 or biosafety level 3.

1.2 Selectivity Index

A selectivity index for a compound is calculated by dividing the 50% cytotoxic concentration ($CC_{50}$) by the 50% inhibitory concentration ($IC_{50}$); the higher the selectivity index for a given drug, the better the prospects for clinical application of the drug. The $CC_{50}$ of a compound is determined by an MTT assay while the $IC_{50}$ a compound is determined by a plaque reduction assay, ultimately yielding the selectivity index of the compound.

1.3 Multi-Cycle Virus Growth Test

MDCK cells were inoculated with an influenza H1N1 virus having a multiplicity of infection (MOI) of 0.002 and then cultured in MEM containing 20 μM of PB2-39 and 1 mg/ml of TPCK trypsin. At 0, 6, 21, 25, 32, 47, and 54 hours following inoculation, the viral supernatant was collected, and the viral titer was determined by a plaque assay.

1.4 Cross-Protection Test

The antiviral effects of each compound disclosed in the present invention against several subtypes of influenza viruses, including H1N1; H3N2; H5N1; H7N7; H7N9; and H9N2, were also tested. In brief, MDCK cells were washed with phosphate buffered saline (PBS) one hour after inoculation with influenza viruses having an MOI of 0.002, and the culture medium was replaced with fresh MEM containing different concentrations (20, 5, 1.25, 0.31 μM) of the compound. Twenty-four hours after inoculation, the cell-free supernatants were collected, and viral titers were determined by reverse transcription real-time quantitative polymerase chain reaction (RT-qPCR).

1.5 Evaluation of the In Vivo Antiviral Effect of the Compound According to the Present Invention In this experiment, BALB/c female mice 6-8 weeks old were used as experimental animals. All the experiments followed the standard operating procedures for animal facilities at biosafety level 3 and were approved by the Animal Ethics Committee of the University of Hong Kong. After anesthesia, a total of 42 mice (14 mice per group) were inoculated with a quantity of influenza virus through the nasal cavity. A drug compound was administered through the nasal cavity starting at 6 hours after inoculation, 2 times a day for 3 days (i.e., 5 doses in all, with 1 dose given on the day of inoculation and 2 doses given on each of the two immediately subsequent days). The first group of mice received 20 μl of 1 mg/ml PB2-39 (i.e., 2.5 mg/kg body weight). The second group of mice received 20 μl of 2.5 mg/ml zanamivir through the nasal cavity as a positive control. The last group of mice received injections of 20 μl of PBS through the nasal cavity as a negative control. The vital signs of the animals were monitored for 21 days or until death. On the fourth day following inoculation, four mice were randomly selected from each group and sacrificed, and their lung tissues were collected. One half of the collected lung tissues from each selected mouse was homogenized, and the supernatant was removed for a determination of viral titer by a plaque assay and RT-qPCR. The remaining half of the lung tissues from each selected mouse was immediately fixed in 10% formalin solution for histopathological analysis. The antiviral effect of PB2-19 on mouse models was evaluated using a method basically the same as that for PB2-39, except that due to limited water-solubility, the dosage of PB2-19 was 1 mg/kg body weight.

2. Results

The $IC_{50}$ and $CC_{50}$ of each compound disclosed in the present invention were determined, and the selectivity index was calculated by dividing the $CC_{50}$ by the $IC_{50}$. In general, the higher the selectivity index for a drug, the better the prospects for clinical application of the drug. Since PB2-19 and PB2-39 showed a selectivity index larger than 100 (Table 1), the two compounds were evaluated in detail in subsequent studies.

TABLE 1

Results of Selectivity Indexes of the Compounds According to the Present Invention

| No. | $IC_{50}$ (μM) | $CC_{50}$ (μM) | Selectivity Index |
| --- | --- | --- | --- |
| PB2-19 | 0.55 ± 0.05 | 150 ± 10 | 273 |
| PB2-35 | 1.24 ± 0.21 | 50 ± 5 | 40 |
| PB2-39 | 1.22 ± 0.23 | >1000 | >819 |

2.1 PB2-39 Provides a Broad-Spectrum Antiviral Effect Against Influenza Virus A

First, the performance of PB2-39 was evaluated in a multi-cycle virus growth test. As shown in FIG. 1A, that compound showed significant effectiveness in fighting influenza virus. For H1N1-subtype influenza virus, the use of 20 μM PB2-39 can reduce the viral titer of supernatant by 100-1000 times. Since the sequence of the PB2 cap-binding domain is highly conserved among influenza viruses of different subtypes, the antiviral effect of PB2-39 on the H5N1, H7N7, H7N9, H9N2, and H3N2 subtypes was further evaluated at the cellular level. As shown in FIG. 1B, PB2-39 inhibited the replication of all the tested influenza strains in a dose-dependent manner. However, viruses of different subtypes had varying sensitivity to PB2-39.

2.2 PB2-39 can Inhibit the Growth of Influenza Virus in Mice

Immediately thereafter, the antiviral effect of PB2-39 in mice was evaluated. First, the survival rates of mice infected with different subtypes of influenza virus after PB2-39 treatment were measured. As shown in FIG. 2A, after mice were inoculated with a $5 \times LD_{50}$ dose (i.e., 5 times the "lethal dose, 50%") of H1N1 virus, all the mice treated with the negative-control PBS died (0% survival rate), while all the mice treated with the positive control (zanamivir) or PB2-39 survived (100% survival rate). When mice were inoculated with a $1 \times LD_{50}$ dose of H5N1 influenza virus, half of the mice treated with the negative-control PBS died (50% survival rate) while all the mice treated with the positive control (zanamivir) or PB2-39 survived (100% survival rate). When mice were inoculated with a $1 \times LD_{80}$ dose of H7N9 virus, 80% of the mice treated with the negative-control PBS died (20% survival rate), while all the mice treated with the positive control (zanamivir) or PB2-39 survived (with a survival rate of 100%). The results showed that PB2-39 can significantly improve the survival rate of mice infected with different influenza viruses. On the fourth day following inoculation, four mice were randomly selected from each group for the collection of lung tissues for the determination of viral load by a plaque assay. As shown in FIG. 2B, treatment with PB2-39 significantly reduced the amounts of viruses in lung tissues. In addition, histopathological examination, as shown in FIG. 2C, further showed improvement with respect to interstitial inflammatory cell infiltration and alveolar injury in the mice treated with PB2-39. The results indicated that PB2-39 can effectively inhibit the replication of influenza virus in mice.

2.3 PB2-19 can Inhibit the Growth of Influenza Virus in Mice

Figure 3:
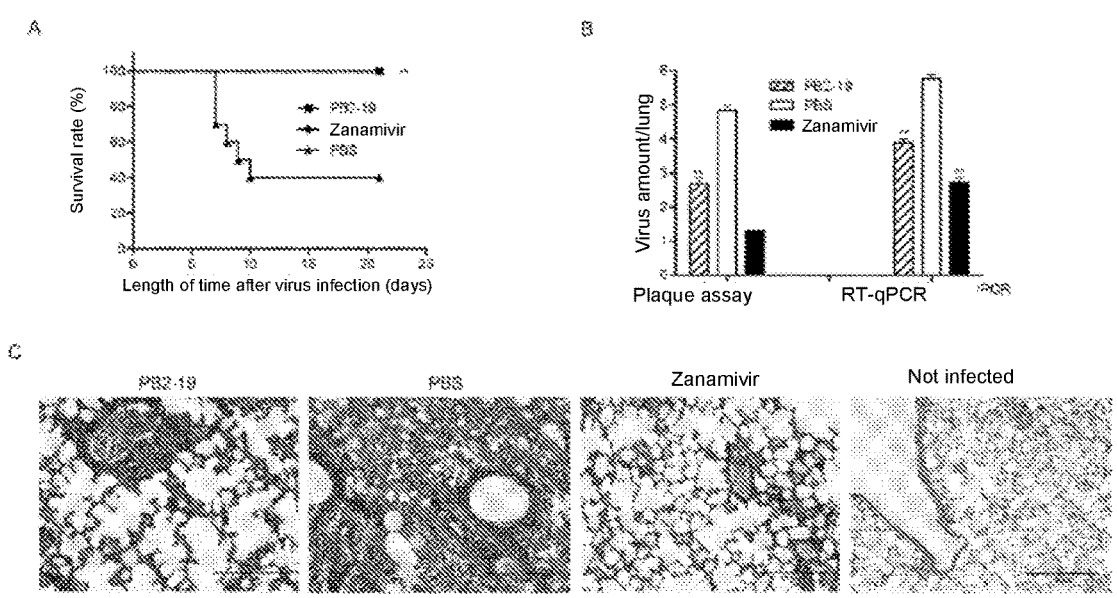

In a previous experiment, the antiviral effect of PB2-19 in mice was also evaluated since PB2-19 also showed good prospects for clinical application by virtue of having a selectivity index of 273 (see Table 1). As shown in FIG. 3, the experimental method was basically the same as that for PB2-39, except that only the antiviral effect of PB2-19 against the H1N1 influenza virus in vivo was evaluated. The results showed that when mice were inoculated with a $1 \times LD_{60}$ dose of H1N1 virus, 60% of the mice treated with the negative-control PBS died (40% survival rate), whereas all the mice treated with the positive control (zanamivir) or PB2-19 survived (100% survival rate) (FIG. 3A). In addition, PB2-19 can also effectively reduce viral proliferation in the lungs of experimental mice (FIG. 3B). Histopathological findings also corroborated the ability of PB2-19 to provide in vivo anti-influenza effects (FIG. 3C).

It should be noted that while the present invention has been particularly described above with reference to preferred embodiments, those of ordinary skill in the art will understand that said embodiments are not intended to limit the present invention and that modifications, equivalent substitutions, and improvements made without departing from the spirit or scope of the present invention shall fall within the scope of the present invention.

What is claimed is:

1. A method of inhibiting the binding of an influenza-virus PB2 subunit to an RNA cap, the method comprising the step of:

exposing the PB2 subunit to a quantity of an antiviral compound;

where the antiviral compound is selected from the group consisting of the following compounds:

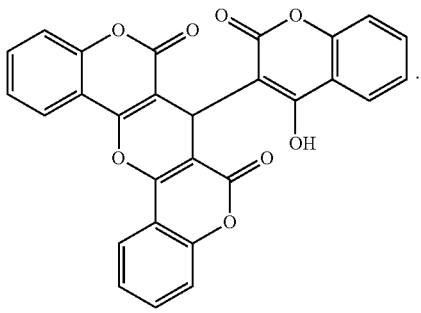

2. A method of treating an influenza-virus infection in a mammal, the method comprising the step of:

administering a quantity of an antiviral compound to the mammal;

where the antiviral compound is selected from the group consisting of the following compounds:

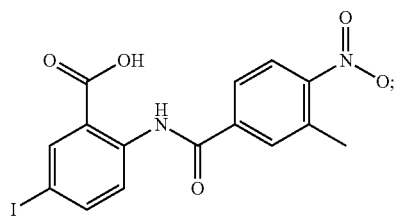

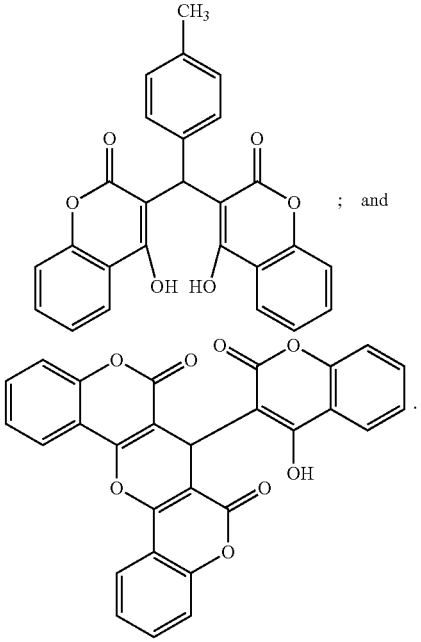

3. The method of claim 2, wherein the mammal is a mouse.

4. The method of claim 2, wherein administering the antiviral compound comprises nasally administering the antiviral compound.

* * * * *